United States Patent [19]

Fina

[11] Patent Number: 4,911,163
[45] Date of Patent: Mar. 27, 1990

[54] TWO BALLOONED CATHETER DEVICE FOR DIAGNOSTIC AND OPERATIVE USE

[76] Inventor: Ernesto Fina, Piazza Leonardo, 10 Viale Ville Maio, I-80129 Napoli NA, Italy

[21] Appl. No.: 214,734
[22] PCT Filed: Jun. 16, 1987
[86] PCT No.: PCT/IT87/00059
  § 371 Date: May 20, 1988
  § 102(e) Date: May 20, 1988
[87] PCT Pub. No.: WO87/07510
  PCT Pub. Date: Dec. 17, 1987

[30] Foreign Application Priority Data

Jun. 12, 1986 [IT] Italy ............................. 29545/86[U]

[51] Int. Cl.⁴ ..................... A61M 29/02; A61B 17/22
[52] U.S. Cl. ................................. 606/127; 604/101; 606/192; 606/108
[58] Field of Search .................. 128/344, 328; 604/96, 604/101, 51–54

[56] References Cited

U.S. PATENT DOCUMENTS

| | | | |
|---|---|---|---|
| 4,295,464 | 10/1981 | Shihata | 128/328 |
| 4,445,892 | 5/1984 | Hussein et al. | 604/101 |
| 4,453,545 | 6/1984 | Inoue | 128/207.15 |
| 4,573,470 | 3/1986 | Samson | 128/344 |
| 4,573,966 | 3/1986 | Weikl et al. | 604/101 |
| 4,636,195 | 1/1987 | Wolinsky | 604/101 X |
| 4,655,746 | 4/1987 | Daniels et al. | 604/53 |

FOREIGN PATENT DOCUMENTS

| | | | |
|---|---|---|---|
| 231748 | 3/1987 | European Pat. Off. | 128/344 |
| 1069823 | 11/1959 | Fed. Rep. of Germany | 128/344 |
| 1460776 | 10/1965 | France | 128/328 |
| 2546757 | 12/1984 | France . | |
| WO8203333 | 10/1982 | PCT Int'l Appl. . | |
| WO8606285 | 11/1986 | PCT Int'l Appl. . | |

*Primary Examiner*—Dalton L. Truluck
*Attorney, Agent, or Firm*—Browdy & Neimark

[57] ABSTRACT

A two ballooned catheter device comprising an inner catheter and an outer catheter slidable one with respect to the other, and a coaxial conduit connected to the proximal end of the outer catheter, a lateral conduit being connected to the outer catheter for introduction of a fluid into a periferal annular space in communication with the balloon of the outer catheter, the inner catheter being connected to the other ballon, and the central annular space between the inner catheter and the outer catheter being in communication with the coaxial conduit, so that a fluid under pressure can be selectively introduced into each balloon and the space between the balloons through the central annular space. The device can be used for confining a sector of a duct or vessel of the body between the two balloons to convey a medicinal or diagnostic fluid into the confined sector or operating through dilation and relaxation of the sector of duct, particularly for the extraction of calculi (FIG. 2).

6 Claims, 2 Drawing Sheets

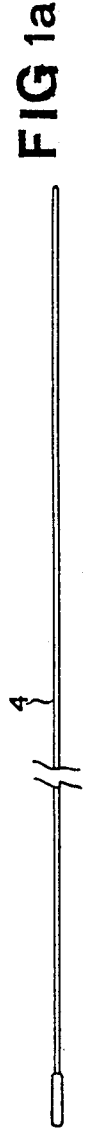
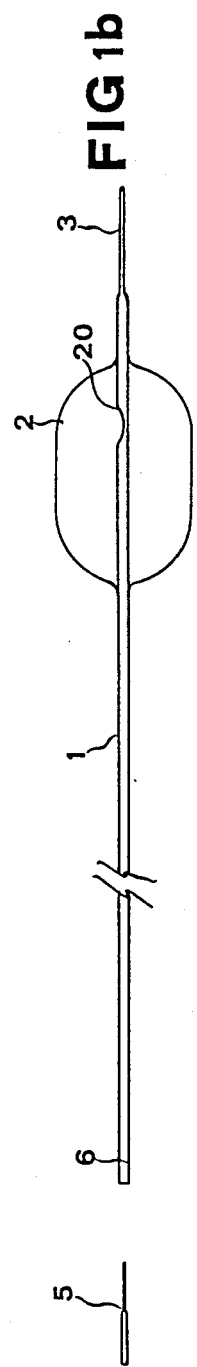
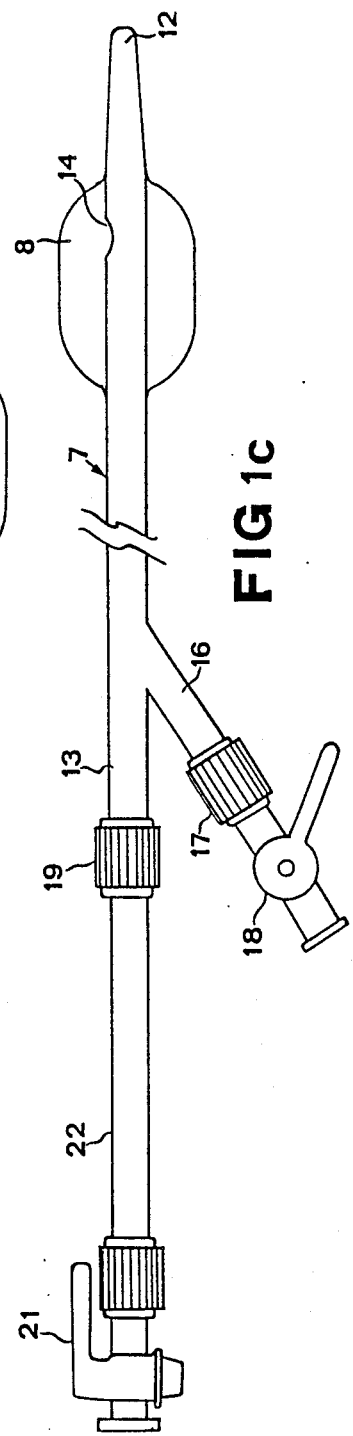

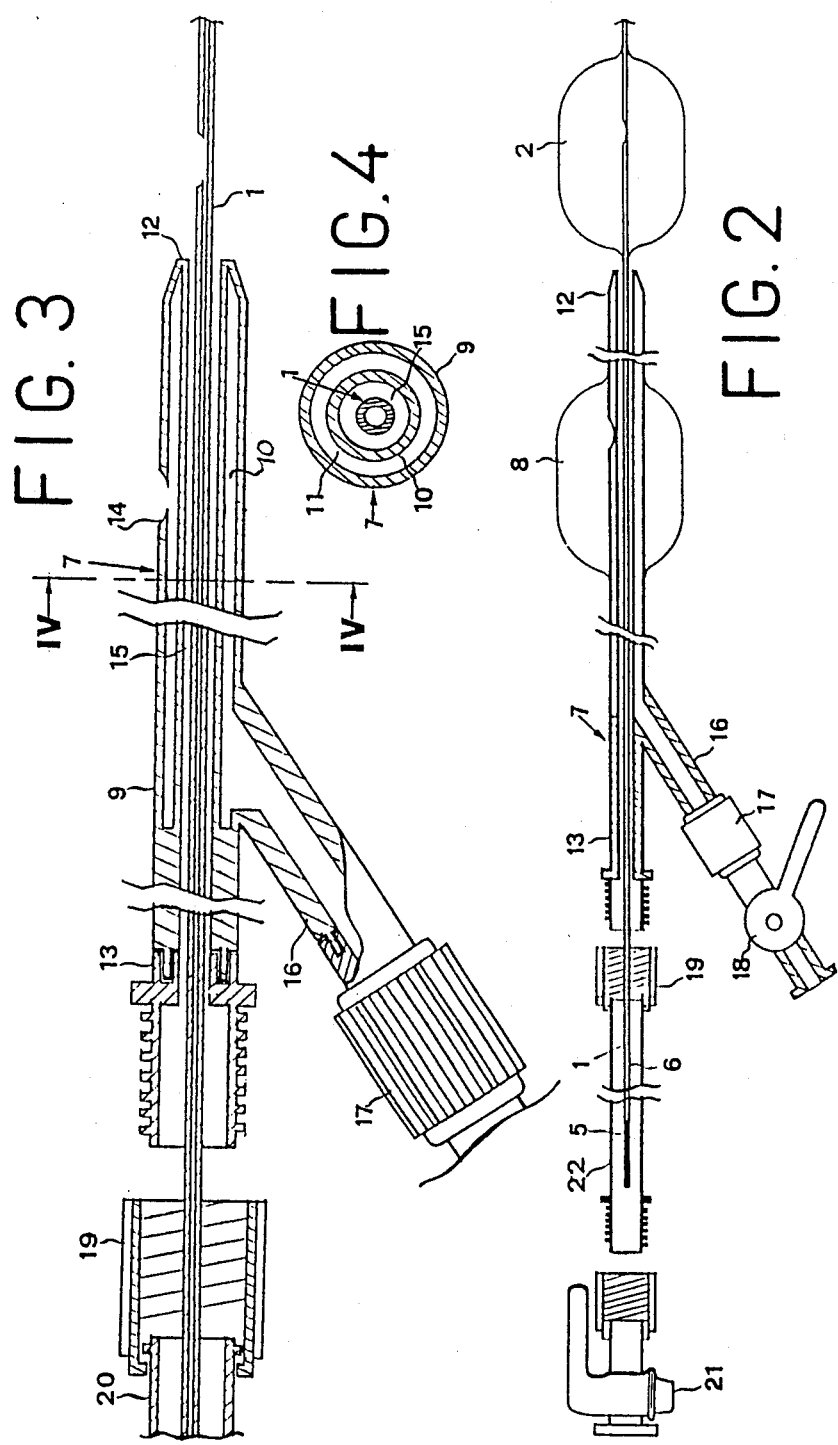

TWO BALLOONED CATHETER DEVICE FOR DIAGNOSTIC AND OPERATIVE USE

BACKGROUND OF THE INVENTION

1. Field of the Invention

The present invention relates to a catheter device for diagnostic, therapeutic and operative use in a duct or vessel of the body of a patient, particularly in ureter and urethra.

The device can be used for radiologic diagnosis in a duct. It can also be used for therapeutic purposes to bring pharmacological substances into a desired sector of a duct. It can also be used advantageously and in particular for removing stones from the urinary passages.

2. Description of the Prior Art

Catheter devices are well known from the prior art for operating in the ureter in order to carry out a mechanical extraction of calculi.

Among said devices, basket and loop catheters, catheters similar to the latter, but provided moreover with a dilator balloon, and catheters with two inflatable balloons are known, as well as a device formed by two catheters sliding one with respect to the other, each having an inflatable balloon at its end.

This catheter is described in U.S. Pat. No. 4,295,464. This device comprises two coaxial catheters, of which the inner and thinner one is introduced, with the balloon deflated, until above the ureter sector in which the calculus is sited. The second catheter, which slides over the first one, is positioned in such a way that its end is below the position of the calculus. Then the balloon which is on the tip below the calculus is inflated. The balloon is inflated gradually until a muscle relaxation of the ureter sector involved is obtained. Successively the balloon of the first catheter is inflated and it is manipulated, also with the aid of strings connected thereto, thus trying to detach the calculus from the wall of ureter sector and cause it to fall downwards. Having obtained this result, the balloon of the second catheter is deflated and brought to a lower position, where it is inflated again. Then the upper catheter is also lowered to try and push the calculus downwards. The above operations are repeated in succession, until the expulsion of the calculus from the orifice of the ureter is obtained. The aforementioned device operates on the calculus by means of a mechanical force which has the function of detaching the calculus from the wall of the ureter and dragging it down. The enlargement of the ureteral passage obtained by the dialating balloon serves the purpose of preparing an easy passage for the calculus, however it has to be observed that it does not act on the ureteral sector in which the calculus is housed, when said calculus remains fixed in its seat. In that case, in fact, the calculus is held blocked to the ureteral wall by an edema which the calculus itself has produced. Consequently a purely mechanical extraction by means of a downwardly directed force on the calculus can produce abrasions and dilaceration of the ureteral wall and very often simply does not succeed.

SUMMARY OF THE INVENTION

An object of the present invention, in the case of extraction of calculi, is to obtain an extirpation of the calculus from the ureteral wall by means of dilation (and eventually contraction) movements of the sector of ureter in which the calculus is fixed, this being obtained by the introduction of a fluid under pressure directly into the ureteral sector in which the calculus is sited, said sector being confined between two inflated balloons which inhibit the same fluid from invading the rest of the urinary passages. This treatment allows the calculus to free itself from the ureteral wall and then to be dragged to the outlet. This treatment cannot be effected by the above described device of the prior art which operates through a mechanical push.

A further object of the present invention is to bring into the area confined between the two inflated balloons, substances to be used for diagnosis, particularly for radiology, as well as medicinal substances which can be confined within the desired sector of the urinary passage. This function is completely independant of the extraction of calculi and it can be applied, for instance, to the entire canal of the ureter or urethra or in particular areas thereof.

The device of the present invention considerably widens the actual diagnostic and therapeutic capabilities attainable with the conventional instrumentation. Further, its use requires an operation which is not very invasive, bloodless, highly efficient and practically without risks.

The efficiency of this method in the extraction of ureteral calculi is grounded on a number of observations of basic importance. A calculus migrating in the ureter stops when it meets a narrow or non-dilatable sector of the passage. Once the calculus has stopped, it lies on the wall producing an edema which further reduces the canal lumen in correspondance with the calculus For this reason the calculus ends by strongly adhering to the ureteral wall and it becomes difficult, if not impossible, to move it either downwards or upwards.

The catheters for extraction of ureteral calculi known from the state of the art can be divided into two large groups: simple extractors (basket or loop) and extractors provided with a balloon for dilation. Those belonging to the first group can be used only in the lower third of the ureter and they are inavoidably damaging to the ureteral mucosa with a possible immediate or delayed injury. Those belonging to the second group are formed by two units: an extractor, basket, loop or balloon, and a dilator. Such instruments have the purpose of being less traumatic than the first group, but they are somewhat inefficient in that they do not deal with the fact that the calculus, for the above mentioned reasons, is rather fixed in the point at which it stops.

The device according to the present invention operates through a completely new mechanism by dilating a more or less extended sector of the ureter containing the calculus and producing the detatchment of the calculus by the mechanical action of dilation, if necessary repeated and alternated to a relaxation of the wall. Only in a few cases is it necessary to resort to using the balloon of the inner catheter to make the movement of the calculus easier. From a diagnostic point of view it allows, moreover, the examination of the ureter and urethra with the nearby organs in a novel and advantageous manner. Additionally, it permits therapeutically active substances and drugs to be brought directly into contact with such structures, restricting such contact only to the desired sectors, protecting the kidney in the upward direction and the bladder in the downward direction for use in the ureter, and the bladder in an upward direction for use in the urethra.

The present invention provides a catheter device for diagnostic and operative use in ducts and vessels of a patient, including an inner catheter in fluid communication with a first balloon fixed to its distal end, and an outer catheter round the first catheter and in fluid communication with a second balloon fixed to its distal end. The first and second catheters being slidable with respect to each other and the inner catheter is substantially coaxial to the outer catheter and provided with a removable plug which closes its proximal end. The first balloon is centered on the distal end of the inner catheter and the outer catheter is formed with coaxial inner and outer walls which define between them an annular periferal space. This annular periferal space is closed at both the distal and proximal ends of the outer catheter and in fluid communication with the second balloon. A central annular space is formed between the outer and the inner catheters, the central annular space being open at both the proximal and distal ends of the outer catheter. The proximal end of the outer catheter is provided with connection means. A lateral conduit for the introduction and extraction of a fluid, in fluid communication with the periferal annular space, is integral with the outer wall of the outer catheter at the proximal end thereof. First valve means is provided on the lateral conduit for controlling a fluid flowing therethrough and a coaxial conduit for fluid introduction and extraction is provided connected by said connection means to the proximal end of the outer catheter and in fluid communication with the central annular space. The coaxial conduit is coaxial to the inner catheter and contains its proximal ends. Second valve means is provided on the coaxial conduit for controlling a fluid flowing therethrough, whereby when a desired sector of a duct or vessel of a patient has been confined between the first and second balloons placed at a preestablished distance and inflated, a fluid under pressure can be introduced into said sector for diagnostic, therapeutic or operative purposes.

BRIEF DESCRIPTION OF THE DRAWINGS

The present invention will be better illustrated with reference to the accompanying drawings, wherein:

FIG. 1a shows a thin metal guide, 1 the inner catheter and 1 the outer catheter with the coaxial conduit connected to it;

FIG. 2 shows the entire catheter device in a cross section;

FIG. 3 shows the catheter device in an enlarged longitudinal cross section; and

FIG. 4 is a cross section along line IV—IV of FIG. 3.

DETAILED DESCRIPTION

Referring to the drawings, the catheter device according to the invention is illustrated in detail. In view of the particular use of the present device for operations effected on the human body, some preferred dimensions of the various parts of the device will also be indicated.

FIG. 1(b) shows the inner catheter, which preferably has a diameter of 1 mm (3 French) and a variable with a flexible tip having a rounded end about 1.5 cm long and a distal end 3 which is X-ray opaque for a length of about 5 cm. At the distal end 3 of the catheter 1, a first inflatable balloon 2 is set, made of an elastic material capable of withstanding a pressure of about 4 atmospheres or more, having a diameter of at least 2 cm when completely inflated. The inner catheter 1 has internally a single central cavity which is used to house a thin metal guide 4 (see FIG. 1 (a)) and simultaneously as an inflating room of the first balloon 2.

A brown coloured line is drawn circumferentially, preferebly at about 70 cm from the tip. Similarly at about 73, 74 and 75 cm from the tip 3 lines are drawn, for example, of yellow, green and blue colour. At about 80 cm from the tip a similar line of red colour is drawn. Said coloured lines help the operator to have a reference point in the operations to be carried out.

In FIG. 1 (b) a plug 5 is also shown for closing the proximal end 6 of the catheter 1, as will be described hereinafter.

Turning now to FIG. 1 (c) an external catheter 7 is shown, having preferably an outer diameter of 4.2 mm (14 French) or less, a variable length and a second inflatable balloon. 8 having the same features as the balloon 2 of the inner catheter 1. As can be seen from FIGS. 3 and 4, the outer catheter 7 is formed with an outer wall 9 and an inner wall 10 between which a peripheral annular space 11 is defined.

The annular space 11 is closed at both the distal end 12 as well as the proximal end 13 of the outer catheter 7. An opening 14 in the outer wall 9 puts the annular space 11 in communication with the interior of the second balloon 8.

The inner wall 10 of the outer catheter 7 defines a longitudinal cavity which runs along the whole catheter 7 from its proximal end 13 to the distal end 12. As the inner catheter 1, as will be described hereinafter, is inserted into the longitudinal cavity of the catheter 7, and a central annular space 15 is defined between the inner catheter 1 and the outer catheter 7.

Near the proximal end 13 of the catheter 7, a lateral conduit 16 is integrally united to the outer wall 9, said lateral conduit 16 being open to the peripheral annular space 11 of catheter 7. The outer catheter 7 consequently has two passages, a central one through the central annular space 15, to enable the inner catheter 1 to penetrate in its interior and a liquid or gas to pass through, and a peripheral passage through the annular space 11, fed by the lateral conduit 16. The lateral conduit 16 is provided with a screw connection 17 of the LUER-LOK ® registered trademark to Becton-Dickinson Inc.) type for a cock 18 of one-through stop-cock type, to enable a fluid to pass for inflating the second balloon 8. The outer catheter 7 moreover is provided with a screw connection 19 of the LUER LOK ® type at its proximal end 13.

The screw connection 19 acts to connect a coaxial conduit 22 formed by a straight tubular section of transparent plastic material, having the same diameter as the outer catheter 7. The coaxial conduit 22 has at the proximal and distal ends, screw connections of the LUER-LOK ® type to enable the connection of the proximal end 13 of the catheter 7 and assembly of a one-through stop-cock 21 at its proximal end. From the foregoing it can be observed that the device according to the present invention shows three routes of fluid flow. The first route goes through the interior of the inner catheter 1 and is in communication with the interior of the first balloon 2 through an opening 20. The second route passes through the lateral conduit 16, the peripheral annular space 11, and the opening 14 to the second balloon 8. A third route is through the coaxial conduit 22, the central annular space 15, and outside the distal end 12 of the outer catheter 7, through the space formed between the first balloon 2 of the inner catheter 1 and the second balloon 8 of the outer catheter 12.

The device according to the present invention allows carrying out of diagnosis, medical treatments and operative functions in a plurality of clinical situations concerning pathologic damages affecting tubular structures such as blood vessels, ducts, ureter, urethra and the like. In fact it is devised to act on a more or less extended sector of a canal, so determining, through the inflation of the balloons 2 and 8, of catheters 1 and 7 respectively, a confinement of this sector from the rest of the canal. A liquid or gas fluid can reach such a confined sector through the central route passing through the coaxial conduit 22 and the central annular space 15, in order to produce a hydraulic dilation of the sector, or to bring medicinal substances into contact with said sector for therapeutic purposes, or to inject a contrast fluid for diagnostic purposes.

EXAMPLES OF USE

Whichever the canal be in which it is used, the device according to the present invention is employed according to the following methods.

The catheter 1 is introduced first, provided with the metal guide 4 in its interior. The catheter 1, having a reduced gauge thanks to the end 3 thinned and rounded in an atraumatic manner, can easily pass over stenotic sections or obstacles, such as calculi, neoformed tissue and the like, possibly present in the duct lumen. Having reached the desired position, the metal guide is withdrawn and the balloon 2 of catheter 1 is inflated by applying a suitable sealed syringe on a sealed junction at the proximal end 6 of the catheter 1. When a desired pressure of inflation has been obtained, the catheter 1 is clamped and the proximal portion exceeding the distance at which the inflated balloons have to be placed in the duct, is cut. To this end, in a particular use of the device of the present invention in the ureter, on the proximal portion of the catheter 1 some lines of different colours are drawn as a reference for carrying out the cutting. After having effected the cutting of catheter 1, a plug 5 is applied at the proximal end 6 and the clamp is removed.

Successively the distal end 12 of the outer catheter 7 is threaded over the proximal end 6 of the catheter 1. The distal end 12 of the catheter 7 has a tapered frustoconical shape. On passing through the central cavity of the catheter 7, catheter 1 forms the central annular space 15.

In the case where the access to the canal is narrow, such as at the junction of ureter and bladder, at cutaneous planum or aponeurotic muscle, for percutaneous access and the like, before applying the catheter 7, it is necessary to proceed with progressive dilations with known dilators which are forwarded along catheter 1 as a guide.

The catheter 7 is stopped in the desired position and the balloon 8 is inflated through the lateral conduit 16 and the periferal annular space 11. In such a way a sector of the canal of a desired length is confined between the two balloons.

Successively the coaxial conduit 22 is connected to the proximal end 13 of the outer catheter 7. By means of the screw connection 19, a syringe is applied to the proximal end of the coaxial conduit 22. It is now possible to inject a therapeutic or diagnostic fluid into the confined sector or canal. The cock 21 at the proximal end of the coaxial conduit 22 enables the liquid to be maintained in situ for a desired time.

At the end of the treatment, the coaxial conduit 22 can be disengaged from the outer catheter 7. Consequently after having withdrawn the fluid from the confined tubular sector, the proximal end 6 of the catheter 1 can be handled. In the case of extraction of calculi, tissue fragments, extraneous bodies, the balloon 2 of the catheter 1 can be used as an extractor. To this end, the plug 5 at the proximal end 6 is withdrawn to produce a partial deflation of the balloon 2 in order to enable a movement of the balloon 2 downwards without encountering resistance.

For withdrawal of the catheter device, after having completely deflated the balloon 2 of the catheter 1 and the balloon 8 of the outer catheter 7, the device can be completely removed.

In order to better clarify the method of use of the catheter device of the present invention, some applications of particular interest will be described in detail.

Extraction of ureteral calculi

The catheter device of the present invention can be employed for the bloodless extraction of ureteral calculi of medium/small size.

For this purpose the inner catheter 1 is first introduced with the metal guide until the calculus is overrun by at least 4 cm, as shown by radiologic control of the X-ray opaque end. The metal guide is removed and a syringe is applied to the proximal end 6 of catheter 1, by means of a sealed junction, for inflating the balloon 2 slowly and gradually until a certain resistance to inflation is felt. The proximal end 6 of catheter 1 is clamped and it is cut in the desired point in correspondance with one of the coloured lines drawn on the catheter. Then the plug 5 is applied and the clamp is removed.

On leaving the catheter 1 in situ with the balloon inflated for an autostatic effect, a series of ureteral dilators of increasing gauge are introduced using the catheter 1 as a guide. Successively the outer catheter 7 is introduced in the same way as the dilators. The introduction is stopped when the proximal end 13 of the catheter 7 coincides with one of the lines drawn on the catheter 1, which will indicate, according to its colour, the distance between the two balloons. The balloon 8 of the catheter 7 is then inflated through the lateral conduit 16.

The coaxial conduit 22 is connected to the proximal end 13 of the catheter 7 and an oily liquid is injected into the ureter area comprised between the two balloons, where the calculus is situated, by means of a sealed syringe applied to the proximal end of the coaxial conduit 22. The patient is made to take a position as inclined as possible on the urologic bed, to cause the calculus to fall downwards by gravity.

In the case of the calculus not immediately dislodging itself from the ureteral wall, it is possible to go on with a cyclic withdrawal of the oily liquid and successive dilation of the ureteral sector. This action of distention and relaxation of the ureteral wall, produced by introducing and withdrawing the liquid in the ureteral sector comprised between the two balloons, will lead in most cases to a dislodgement of the calculus from the ureteral wall, even when the calculus has been settled for a long time in that seat and has produces flogistic and edematous alterations of the wall. If necessary, the balloon 2 of the catheter 1 can also be used as an extractor.

After having obtained the dilation of the ureteral sector in which the calculus is seated, the coaxial conduit 22 is disengaged from the catheter 7 and after removing the plug 5 from the proximal end 6 of the catheter 1, traction is carefully applied on the catheter 1, starting the movement downwards when the balloon has been deflated to reduce its volume so that it can slide in the ureteral lumen with a minimum amount of friction. The plug 5 is then applied again and the catheter 1 is drawn downwards, until the balloon 2 of the catheter 1 stops at the end of the catheter 7. In this position, the proximal end 13 of the catheter 7 will be in correspondance with a line drawn on the catheter 1. To make the calculus proceed downwards until it comes out of the ureteral meatus, the balloon 2 of the catheter 1 is inflated again and the outer catheter 7 is pulled downwards after having its balloon 8 deflated. The balloon 8 is inflated again when it is at a desired distance from the balloon 2 of the catheter 1 and the operation is progressively repeated. In correspondance with the ureteral meatus, the balloon 8 of the outer catheter 7 can be employed as a dilator of the papilla.

Use for diagnosis and endo-ureteral therapy

The catheter device of the present invention can be used for a radiologic diagnosis of the whole ureter or a portion thereof. For a diagnosis of the whole ureter the procedure is like that of an extraction of calculi as above described, blocking the balloon 2 of the catheter 1 in a subjunctional seat and the balloon 8 of the catheter 7 in correspondance with the ureter and bladder junction. A sealed syringe is applied to the proximal end of the coaxial conduit 22 and a contrast medium is injected at a desired pressure for displaying the whole canal so as to put into evidence some very important features, such as the distension ability and the elasticity of the wall, the presence of angulations or fixed points, the presence of not distensible stenotic portions, and/or the presence of any fistula or solution of continuity.

The method of double contrast (liquid and gas) can also be used with success, by withdrawing the liquid medium after injection thereof and by insufflating air. This makes it possible to detect highly mucose irregularities and eventual urothelium papilloma, and to make a precise differential diagnosis of the defects of ureteral filling between X-ray transparent calculi and urothelium papilloma (double contrast ureterography).

The same method can be applied in the same way to a more restricted sector of the canal, where an injury has been already detected (fistulous confluence of traumatic delaceration).

The two balloon catheter device can be therapeutically used for determining the hydraulic dilation of stenotic portions and to bring drugs, such as cortisone, anti-plastics and the like, into contact with portions thereof. For such use the catheter can be held in situ for the time of treatment without hampering the urinary drain by maintaining only the balloon of the outer catheter 7 partially inflated.

Diagnostics and endo-urethral therapy

The catheter device can be advantageously used for diagnosis of urethra in men and women. By following the above described method a contrast medium can be injected into the canal or part thereof. Stenosis, fistulae, diverticula which cannot be displayed by the conventional methods can thus be evidenced. The uretro-prostatic and uretro-deferental reflux can also be observed, featured by the contrast display of the deferens and prostate gland ducts.

In the therapeutic field, solutions can be injected containing drugs for the treatment of flogistic processes affecting the rear urethra and the prostate.

The device can also be used for the hydraulic dilation of stenotic segments.

I claim:

1. Catheter device for use in the ureteral tract of a patient including an inner catheter in fluid communication with a first balloon fixed at its distal end and an outer catheter which embraces said inner catheter and in fluid communication with a second balloon fixed at its distal end, said first and second catheters being slidable one with respect to the other, said catheter device comprising in combination:

said inner catheter being substantially coaxial to said outer catheter and having an inner central cavity, a flexible tip and a diameter of about 3 French (1 mm);

a thin metal guide slidably inserted in said inner central cavity of said catheter, to be extracted when said inner catheter is positioned in the ureter;

said first balloon being concentrically fixed on the distal end of the inner catheter;

said outer catheter being formed with coaxial inner and outer walls which define therebetween a peripheral annular space, said peripheral annular space being closed at both the distal and proximal ends of said outer catheter and being in fluid communication with said second balloon, a central annular space being formed between said outer catheter and said inner catheter, said central annular space being open at both the distal proximal end of said outer catheter being provided with connection means said outer catheter to be inserted into the ureter in a sliding relation ship to said inner catheter;

a lateral conduit in fluid communication with said peripheral annular space, integral with said outer wall of the outer catheter in correspondence with said proximal end;

first valve means on said lateral conduit for controlling a fluid flowing therethrough;

a coaxial conduit connected to said proximal end of the outer catheter through said connection means, in fluid communication with said central annular space, said coaxial conduit being coaxial to the inner catheter and containing the proximal end thereof;

second valve means on said coaxial conduit for controlling a fluid flowing therethrough, whereby, when the desired sector of the ureteral tract has been confined between said first and second balloons, place at a desired distance one from the other and inflated, a fluid under pressure can be introduced into said sector, for dilating the tract.

2. A device according to claim 1, wherein said first and second valve means are stop cocks.

3. A device according to claim 1, wherein said outer catheter (7) has an outer diameter of about 14 French (4,2 mm).

4. A method for extracting from the ureteral tract of a patient, a stone which is held fixed by the wall of the ureteral tract, comprising:

(a) confining a sector of the ureteral tract wherein the calculus is fixed, between two inflated balloons which adhere to the wall of said sector;

(b) introducing the fluid under pressure into said sector for dilating the wall of the ureteral tract in said sector;

(c) withdrawing said fluid from said sector to relax the wall in said sector;

(d) repeating the operation of introducing and withdrawing the fluid, until the calculus is removed from said wall;

(e) and repeating the operations (a) to (d) in progressively lower sectors of the ureteral tract to bring the calculus to the outlet of the ureteral tract.

5. A method according to claim 4, in which said balloons are inflated at a pressure to about 4 atmospheres.

6. A method according to claim 4, in which an outer catheter carrying one of said balloons is inserted into the ureter by a sliding movement along an inner catheter carrying the other of said balloons, acting as a guide.

* * * * *